(12) United States Patent
Herrmann et al.

(10) Patent No.: US 7,621,948 B2
(45) Date of Patent: Nov. 24, 2009

(54) PERCUTANEOUS HEART VALVE

(75) Inventors: Howard C Herrmann, Bryn Mawr, PA (US); Nilesh Mankame, Ann Arbor, MI (US); Suresh G. K. Ananthasuresh, Bangalore (IN)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 646 days.

(21) Appl. No.: 10/565,142

(22) PCT Filed: Jul. 20, 2004

(86) PCT No.: PCT/US2004/023211

§ 371 (c)(1),
(2), (4) Date: Jun. 29, 2006

(87) PCT Pub. No.: WO2005/009285

PCT Pub. Date: Feb. 3, 2005

(65) Prior Publication Data

US 2007/0016286 A1    Jan. 18, 2007

Related U.S. Application Data

(60) Provisional application No. 60/488,838, filed on Jul. 21, 2003.

(51) Int. Cl.
*A61F 2/24* (2006.01)
(52) U.S. Cl. ........................ 623/2.1; 623/2.33
(58) Field of Classification Search .......... 623/2.1–2.38
See application file for complete search history.

(56) References Cited

U.S. PATENT DOCUMENTS 4,056,854 A    11/1977   Boretos et al. .................. 3/1.5

(Continued)

FOREIGN PATENT DOCUMENTS

| CA | 1 232 4007 | 2/1988 |
| WO | WO 96/02212 | 2/1996 |
| WO | WO 00/44311 | 8/2000 |

(Continued)

OTHER PUBLICATIONS

Davies, H., "Catheter-Mounted Valve For Temporary Relief of Aortic Insufficiency," The Lancet, Jan. 30, 1965.

(Continued)

*Primary Examiner*—Suzette J Gherbi
(74) *Attorney, Agent, or Firm*—McCarter & English, LLP

(57) ABSTRACT

A percutaneously inserted bistable heart valve prosthesis is folded inside a catheter for transseptal delivery to the patient's heart for implantation. The heart valve has an annular ring, a body member having a plurality of legs, each leg connecting at one end to the annular ring, claws that are adjustable from a first position to a second position by application of external force so as to allow ingress of surrounding heart tissue into the claws in the second position, and leaflet membranes connected to the annular ring, the body member and/or the legs, the leaflet membranes having a first position for blocking blood flow therethrough and a second position for allowing blood flow therethrough. The heart valve is designed such that upon removal of the external force the claws elastically revert to the first position so as to grip the heart tissue positioned within the claws, thereby holding the heart valve in place. The body member and claws may be integrated into a one-piece design. The heart valve may be used as a prosthesis for the mitral valve, aortic valve, pulmonary valve, or tricuspid valve by adapting the annular ring to fit in a respective mitral, aortic, pulmonary, or tricuspid valve opening of the heart.

15 Claims, 12 Drawing Sheets

U.S. PATENT DOCUMENTS

| | | | |
|---|---|---|---|
| 4,733,665 A * | 3/1988 | Palmaz | 606/108 |
| 4,759,759 A | 7/1988 | Walker et al. | 623/2 |
| 4,777,951 A | 10/1988 | Cribier et al. | |
| 5,554,185 A | 9/1996 | Block et al. | 623/2 |
| 5,575,818 A * | 11/1996 | Pinchuk | 623/1.15 |
| 5,843,161 A * | 12/1998 | Solovay | 623/1.13 |
| 5,855,601 A | 1/1999 | Bessler et al. | 623/2 |
| 6,007,574 A * | 12/1999 | Pulnev et al. | 623/1.15 |
| 6,183,494 B1 | 2/2001 | Amor et al. | 606/198 |
| 6,309,415 B1 * | 10/2001 | Pulnev et al. | 623/1.22 |
| 6,425,916 B1 | 7/2002 | Garrison et al. | 623/2.11 |
| 6,454,799 B1 | 9/2002 | Schreck | 623/2.18 |
| 6,458,153 B1 | 10/2002 | Bailey et al. | 623/1.24 |
| 6,461,366 B1 | 10/2002 | Segiun | 606/144 |
| 6,482,228 B1 | 11/2002 | Norred | 623/2.17 |
| 6,494,909 B2 | 12/2002 | Greenhalgh | 623/1.24 |
| 6,517,576 B2 | 2/2003 | Gabbay | 623/2.14 |
| 6,537,314 B2 | 3/2003 | Langberg et al. | 623/2.36 |
| 6,551,344 B2 | 4/2003 | Thill | 606/213 |
| 6,561,969 B2 | 5/2003 | Frazier et al. | 600/16 |
| 6,582,462 B1 | 6/2003 | Andersen et al. | 623/1.26 |
| 6,605,102 B1 | 8/2003 | Mazzocchi et al. | 606/200 |
| 6,629,534 B1 | 10/2003 | St. Goar et al. | 128/898 |
| 6,641,557 B1 | 11/2003 | Frazier et al. | 604/115 |
| 6,641,608 B1 * | 11/2003 | Pulnev | 623/1.15 |
| 6,650,923 B1 | 11/2003 | Lesh et al. | 600/407 |
| 6,736,845 B2 | 5/2004 | Marquez | |
| 6,846,325 B2 | 1/2005 | Liddicoat | |
| 6,893,459 B1 * | 5/2005 | Macoviak | 623/2.11 |
| 6,896,690 B1 | 5/2005 | Lambrecht | |
| 6,908,478 B2 | 6/2005 | Alferness et al. | |
| 6,951,571 B1 * | 10/2005 | Srivastava | 623/1.24 |
| 6,974,476 B2 | 12/2005 | McGuckin | |
| 7,033,390 B2 | 4/2006 | Johnson | |
| 7,041,132 B2 | 5/2006 | Quijan | |
| 7,097,659 B2 | 8/2006 | Woolfson | |
| 7,160,323 B2 * | 1/2007 | Pulnev et al. | 623/6.22 |
| 7,311,730 B2 * | 12/2007 | Gabbay | 623/2.38 |
| 7,316,712 B2 | 1/2008 | Peredo | |
| 7,320,704 B2 | 1/2008 | Lashinski et al. | |
| 7,419,502 B2 * | 9/2008 | Pulnev et al. | 623/1.22 |
| 7,419,503 B2 * | 9/2008 | Pulnev et al. | 623/1.22 |
| 7,569,062 B1 * | 8/2009 | Kuehn et al. | 606/139 |
| 2001/0002445 A1 | 5/2001 | Vesely | 623/2.11 |
| 2002/0133226 A1 | 9/2002 | Marquez et al. | |
| 2002/0138138 A1 | 9/2002 | Yang | 623/2.18 |
| 2004/0024451 A1 | 2/2004 | Johnson et al. | |
| 2004/0034411 A1 | 2/2004 | Quijano et al. | |
| 2004/0044406 A1 | 3/2004 | Woolfson et al. | |
| 2004/0092858 A1 | 5/2004 | Wilson et al. | |
| 2004/0097979 A1 | 5/2004 | Svanidze | |
| 2004/0127981 A1 | 7/2004 | Rahdert | |
| 2004/0127982 A1 | 7/2004 | Machold | |
| 2004/0138745 A1 | 7/2004 | Macoviak | |
| 2004/0186563 A1 | 9/2004 | Iobbi | |
| 2004/0210304 A1 | 10/2004 | Seguin | |
| 2004/0225353 A1 | 11/2004 | McGuckin, Jr. | |
| 2004/0260393 A1 | 12/2004 | Rahdert | |
| 2005/0033398 A1 | 2/2005 | Seguin | |
| 2005/0049692 A1 | 3/2005 | Numamoto | |
| 2005/0055089 A1 | 3/2005 | Macoviak | |
| 2005/0075584 A1 | 4/2005 | Cali | |
| 2005/0182486 A1 | 8/2005 | Gabbay | |
| 2005/0216079 A1 | 9/2005 | Macoviak | |
| 2005/0261759 A1 | 11/2005 | Lambrecht | |
| 2005/0273160 A1 | 12/2005 | Lashinski et al. | |
| 2006/0015179 A1 | 1/2006 | Bulman-Fleming et al. | |
| 2006/0020327 A1 | 1/2006 | Lashinski et al. | |
| 2006/0020332 A1 | 1/2006 | Lashinski et al. | 623/2.11 |
| 2006/0020333 A1 | 1/2006 | Lashinski et al. | |
| 2006/0020334 A1 | 1/2006 | Lashinski et al. | |
| 2006/0025854 A1 | 2/2006 | Lashinski et al. | |
| 2006/0025855 A1 | 2/2006 | Lashinski et al. | |
| 2006/0089671 A1 | 4/2006 | Goldfarb et al. | |
| 2006/0161249 A1 | 7/2006 | Realyvasquez et al. | |
| 2006/0253191 A1 | 11/2006 | Salahieh et al. | |
| 2007/0005133 A1 | 1/2007 | Lashinski et al. | |
| 2008/0015687 A1 | 1/2008 | Lashinski et al. | |
| 2008/0208332 A1 * | 8/2008 | Lamphere et al. | 623/2.38 |
| 2008/0221672 A1 * | 9/2008 | Lamphere et al. | 623/2.12 |

FOREIGN PATENT DOCUMENTS

| | | |
|---|---|---|
| WO | WO 01/49213 | 7/2001 |
| WO | WO 02/41789 | 5/2002 |
| WO | WO 03/088873 | 10/2003 |
| WO | WO 2004/043293 | 1/2004 |
| WO | WO 2004/019811 | 3/2004 |
| WO | WO 2004/028558 | 4/2004 |
| WO | WO 2004/030568 | 4/2004 |
| WO | WO 2004/030569 | 4/2004 |
| WO | WO 2004/030570 | 4/2004 |
| WO | WO 2004/112657 | 12/2004 |
| WO | WO 2005/112827 | 1/2005 |
| WO | WO 2005/009285 | 2/2005 |
| WO | WO 2005/046528 | 5/2005 |

OTHER PUBLICATIONS

Block, P.C., "Percutaneous mitral valve repair for mitral regurgitation," *J. of Interventional Cardiology,* 2003, 16(1), 93-96.

Bonhoeffer, et al., "Percutaneous insertion of the pulmonary valve," *J. of the Am. College of Cardiology,* 2002, 39(10), 1664-1669.

Cribier, et al., "Percutaneous transcatheter implantation of an aortic valve prosthesis for calcific aortic stenosis," *Circulation,* 2002, 3006-3008.

PCT International Search Report dated Feb. 9, 2005.

PCT International Search Report dated Aug. 8, 2008 (PCT/US08/50096).

PCT International Search Report dated Aug. 8, 2008 (PCT/US08/54410).

PCT International Search Report dated Aug. 12, 2008.

European Search Report dated Apr. 4, 2007.

* cited by examiner

PERCUTANEOUS HEART VALVE

CROSS-REFERENCE TO RELATED APPLICATIONS

The present patent application claims priority to U.S. Provisional Patent Application Ser. No. 60/488,838, filed Jul. 21, 2003, the contents of which are hereby incorporated by reference in their entirety.

FIELD OF THE INVENTION

The present invention is directed to a design for a percutaneously inserted bistable heart valve prosthesis that may be folded inside a catheter for delivery to the mitral valve and other valves of the heart for implantation.

BACKGROUND OF THE INVENTION

Heart valve regurgitation occurs when the heart valve does not close completely as a result of disease or injury. Pulmonary valve regurgitation has been shown to increase a patient's susceptibility to arrhythmias, sudden death and right ventricular dysfunction. Similarly, mitral regurgitation due to ischemic and degenerative (prolapse) disease has been shown to contribute to left ventricular dysfunction due to remodeling, and to left ventricular dilation, resulting in worsening of the mitral regurgitation. Currently, malfunctioning heart valves are usually replaced with biologic or mechanical prostheses through open-heart surgery with the attendant significant risk of death, stroke, infection, bleeding, and complications due to the use of general anesthesia and cardiopulmonary bypass. Such procedures also have significant potential for a long recovery period. However, for certain disease states, percutaneous alternatives have been used in place of open-heart surgery due to the lower morbiaity and mortality. For instance, rheumatic mitral stenosis, a condition in which the mitral valve does not open properly, has been treated by inserting a balloon from the femoral vein to enlarge the mitral valve opening.

Based on the success of percutaneous balloon valvuplasty for mitral stenosis, investigators have explored other alternative methods to treat valvular heart disease without surgery. For example, Cribier et al. describe in a report entitled "Percutaneous Transcatheter Implantation of an Aortic Valve Prosthesis for Calcific Aortic Stenosis," *Circulation*, Dec. 10, 2002, pages 3006-3008, a balloon-expandable stent to which a biologic valve prosthesis is sewn. This device is utilized to treat calcific aortic stenosis. In an article entitled "Percutaneous Insertion of the Pulmonary Valve," *Journal of the American College of Cardiology*, Vol. 39, No. 10, May 15, 2002, pages 1664-1669, Bonhoeffer et al. describe a similar stent approach with a bovine venous (jugular) valve inserted to treat pulmonic valve disease. Others are developing repair techniques for mitral valve disease that involve placing a clip on the mitral leaflets (U.S. Pat. No. 6,629,534), cinching the mitral annulus from the coronary sinus (U.S. Pat. No. 6,537,314), or deploying an inflatable heart valve that is mechanically held in place (U.S. Pat. No. 5,554,185).

Norred (U.S. Pat. No. 6,482,228) discloses a percutaneous aortic valve replacement in which a heart valve prosthesis having ribs and a circular elastomeric canopy is folded for insertion into a catheter for delivery to the implantation region without surgery. Once in the ascending aorta, the body and leaflets of the heart valve prosthesis are opened like an umbrella by pulling on a central column of suture-like members. Hinge joints are used to create a miniature umbrella. However, the aortic valve prosthesis is anchored using a stent system that is extended in the ascending aorta to anchor the valve in the aortic channel above the biologic aortic valve. The suture-like members used to open the umbrella structure are deployed as part of the stent system. Such a design is not amenable to placement of the heart valve prosthesis at the location of the biologic valve.

Other stented heart valve prostheses are described in the art in which the anchoring system is a passive one that requires either balloon expandable stents or a self-expanding stent design. For example, such stented designs are described in U.S. Pat. No. 6,454,799, U.S. 2002/0138138, U.S. Pat. No. 6,582,462, U.S. Pat. No. 6,458,153, U.S. Pat. No. 6,425,916, and U.S. Pat. No. 5,855,601. It will be appreciated that once these stented heart valve prostheses are deployed, they cannot be repositioned, refolded, or easily removed. Furthermore, the rigidity of the stent as it is deployed in calcified positions may allow for regurgitation around the outside of the stent, as has been seen in the early aortic valve deployments which utilize this design. It is also difficult to position these designs as one has to inflate a balloon in a moving column of blood white the heart is beating and one only gets one chance to accurately deploy it.

An additional difficulty occurs when deploying a stented heart valve in an annulus that is not thickened by calcium. The stent design lends itself slightly better to the aortic position where the height of the annulus has been increased and the width thickened by the presence of calcium in calcific aortic stenosis. However, when calcium is not present, as in other causes of aortic valve disease and in the mitral position, the stent may be difficult to anchor on the relatively thin annulus. Furthermore, the nature by which the stent folds on a balloon and then expands with plastic deformability limits the ratio of its initial to final size such that it will, by necessity, have a fairly large profile making percutaneous insertion via catheter more difficult in a valve annulus with a large diameter that has not been reduced by calcium deposition.

An improved heart valve prosthesis design is desired that utilizes a folding structure that allows a low profile for insertion via a catheter and a large profile once deployed but without use of a balloon or stent, thereby allowing a smaller to larger profile range. A heart valve prosthesis design is also desired that can be deployed, folded, removed, and then redeployed so as to increase the safety as well as the preciseness of the deployment. The present invention addresses these and other needs in the heart valve prosthesis art.

SUMMARY OF THE INVENTION

The present invention addresses these and other needs in the heart prosthesis art by providing a percutaneously inserted bistable heart valve prosthesis that may be folded inside a catheter for delivery to the patient's heart for implantation. The heart valve has an elastic annular ring, a body member having a plurality of legs, each leg connecting at one end to the annular ring, claws that are adjustable from a first position to a second position by application of external force so as to allow ingress of surrounding heart tissue into the claws in the second position, and leaflet membranes connected to the annular ring, the body member and/or the legs, the leaflet membranes having a first position for blocking blood flow therethrough and a second position for allowing blood flow therethrough. The heart valve is designed such that upon removal of the external force the claws elastically revert to the first position so as to grip the heart tissue positioned within the claws, thereby holding the heart valve in place. The body member and claws may be integrated into a one-piece design. The heart valve so designed may be used as a prosthesis for the mitral valve, aortic valve, pulmonary valve, or tricuspid valve by adapting the annular ring to fit in a respective mitral, aortic, pulmonary, or tricuspid valve opening of the heart.

In an exemplary embodiment of the heart valve, the annular ring, the body member, the legs, the claws and the leaflet membranes fold into a collapsed position for insertion into a catheter for percutaneous delivery to the heart for implantation. The heart valve has a first stable position after passage through the catheter and a second stable position to which the heart valve is forced for implantation. In the second stable position, the body member pushes outward on the annular ring to assist anchoring the heart valve in the heart tissue. The elastic annular ring also may be expandable so as to expand to anchor the heart valve at the implantation position in the valve cavity.

Each claw is connected to the annular ring and/or a leg to permit movement of each claw from a first claw position to a second claw position. Movement of the claws is controlled remotely during the implantation procedure by filaments extending proximally from the heart valve and connecting the body member to the claws.

The scope of the present invention also includes a method of implanting a bistable percutaneous heart valve at an implantation position (heart valve cavity) of a patient. An exemplary embodiment of such a method includes the steps of:

folding the bistable percutaneous heart valve into a collapsed position;

inserting a catheter into a patient and guiding a distal end of the catheter to a position adjacent the implantation position in the patient's heart;

inserting the folded heart valve into the catheter and advancing the folded heart valve to the distal end of the catheter;

guiding the folded heart valve beyond the distal end of the catheter so as to cause the heart valve to elastically unfold to a stable unfolded position;

forcing the unfolded heart valve into a second stable position guiding the heart valve to the implantation position;

adjusting claws of the heart valve by the application of an external force so as to allow ingress of surrounding heart tissue into the claws, whereupon removal of the external force the claws elastically revert to a more closed position so as to grip the heart tissue positioned within the claws, thereby holding the heart valve in place; and removing the guiding device and the catheter.

The external force applied to adjust the claws is provided by manipulating at a proximal end of the catheter filaments that passes through the catheter and connect at a distal end to the claws. The filaments may also be used to switch the heart valve between its two stable configurations and to open the claws. The filaments are removed once implantation is completed or may be left in the heart valve prosthesis, drawn close to the body member of the heart valve prosthesis so as not to impede blood flow. Separate fixed length filaments attach one side of a claw to a leg of the body member so that when the longer filaments are pulled beyond a certain point the claws are opened further.

A significant benefit of such a method is that the steps of guiding the unfolded heart valve to the implantation position and adjusting the claws to hold the heart valve in place may be repeated until the position, stability and functioning of the heart valve are satisfactory. Also, by forming the heart valve from elastic materials, the heart valve may push outward on the heart tissue in the stable unfolded position so as to assist anchoring the heart valve in the heart tissue.

BRIEF DESCRIPTION OF THE DRAWINGS

The present invention will be apparent from the following detailed description of the invention in conjunction with the accompanying drawings, of which.

DETAILED DESCRIPTION OF ILLUSTRATIVE EMBODIMENTS

The invention will be described with reference to FIGS. 1-12. Those skilled in the art will appreciate that the description given herein with respect to these figures is for exemplary purposes only and is not intended in any way to limit the scope of the invention. All questions regarding the scope of the invention may be resolved by referring to the appended claims.

The heart valve described herein has a triangular-based bistable compliant structure that forms the housing for valve leaflets made of standard biologic or artificial prosthetic material, such as cryo or chemically preserved bovine pericardium. The structure is folded inside a catheter for transseptal delivery to the mitral valve cavity or by direct venous or arterial delivery to the aortic valve, pulmonary valve, or tricuspid valve cavities. The folded structure is advanced through the catheter by, for example, a smaller diameter guide catheter, to the implantation position (e.g., left atrium for mitral valve) where the structure is deployed inside the diseased valve. The structure opens to a first stable position when it emerges from the distal end of the catheter and is forced into a second stable position by pulling actuating filaments. The structure is then anchored on the annulus at multiple (e.g., 3) points. It will be appreciated that this design and implantation methodology does not require surgery and that the bistable anchoring structure allows for strong, stable implantation, central blood flow, and a stable platform for the valve leaflets. Moreover, positioning can be more precise than with a balloon expandable device, such as a stent, and, unlike a stent, the positioning may be repeated until the desired implantation is accomplished. The heart valve structure described herein also allows anchoring to the valve annulus in states where a stent would not have sufficient tissue to adhere, as in the case of mitral valve disease.

In an exemplary embodiment, the heart valve prosthesis is designed to be placed at the site of a diseased heart valve, as distinct from existing heart valve prostheses designs that use stents that are placed in the connecting blood vessels. As a result, the ability of the operator to be able to reposition and re-anchor the heart valve in order to more accurately position the heart valve in the heart valve opening is of increased significance.

Figure 1A:
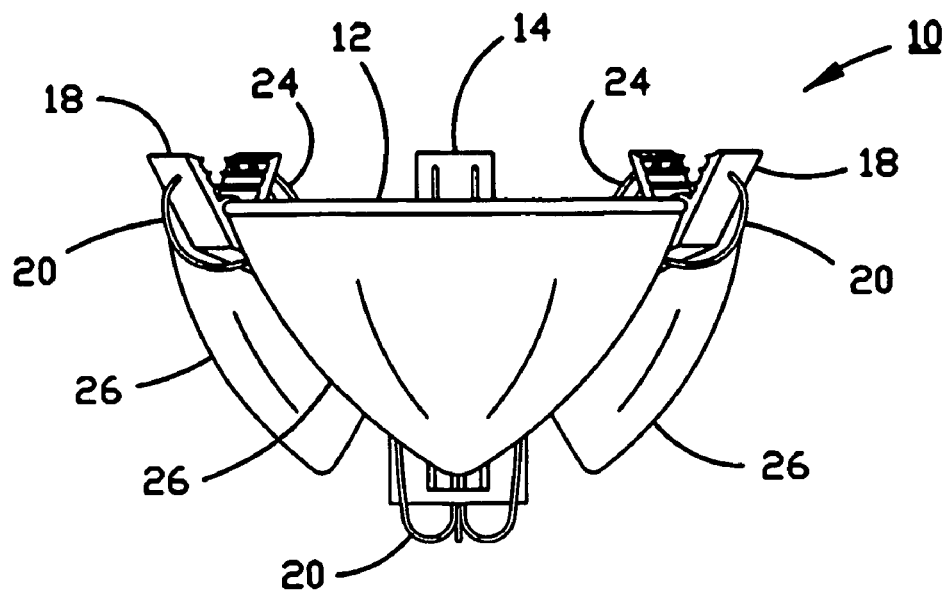
FIG. 1A illustrates a side view of a bistable heart valve prosthesis in accordance with an embodiment of the invention.
Figure 1B:
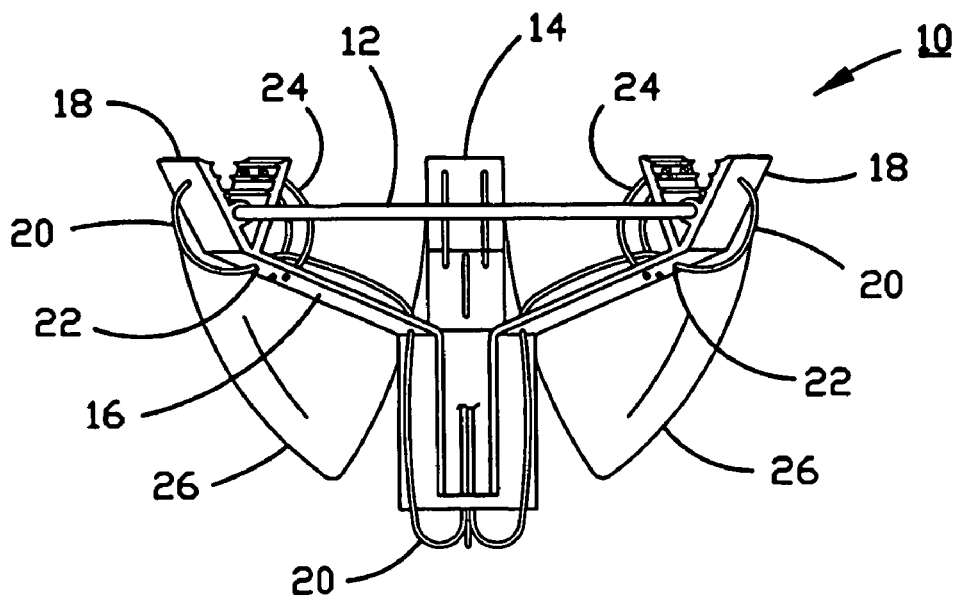
FIG. 1B illustrates the bistable heart valve prosthesis of FIG. 1A with a leaflet cut away so that the body member, legs, annular ring, claws, and filaments may be seen more clearly.
Figure 4:
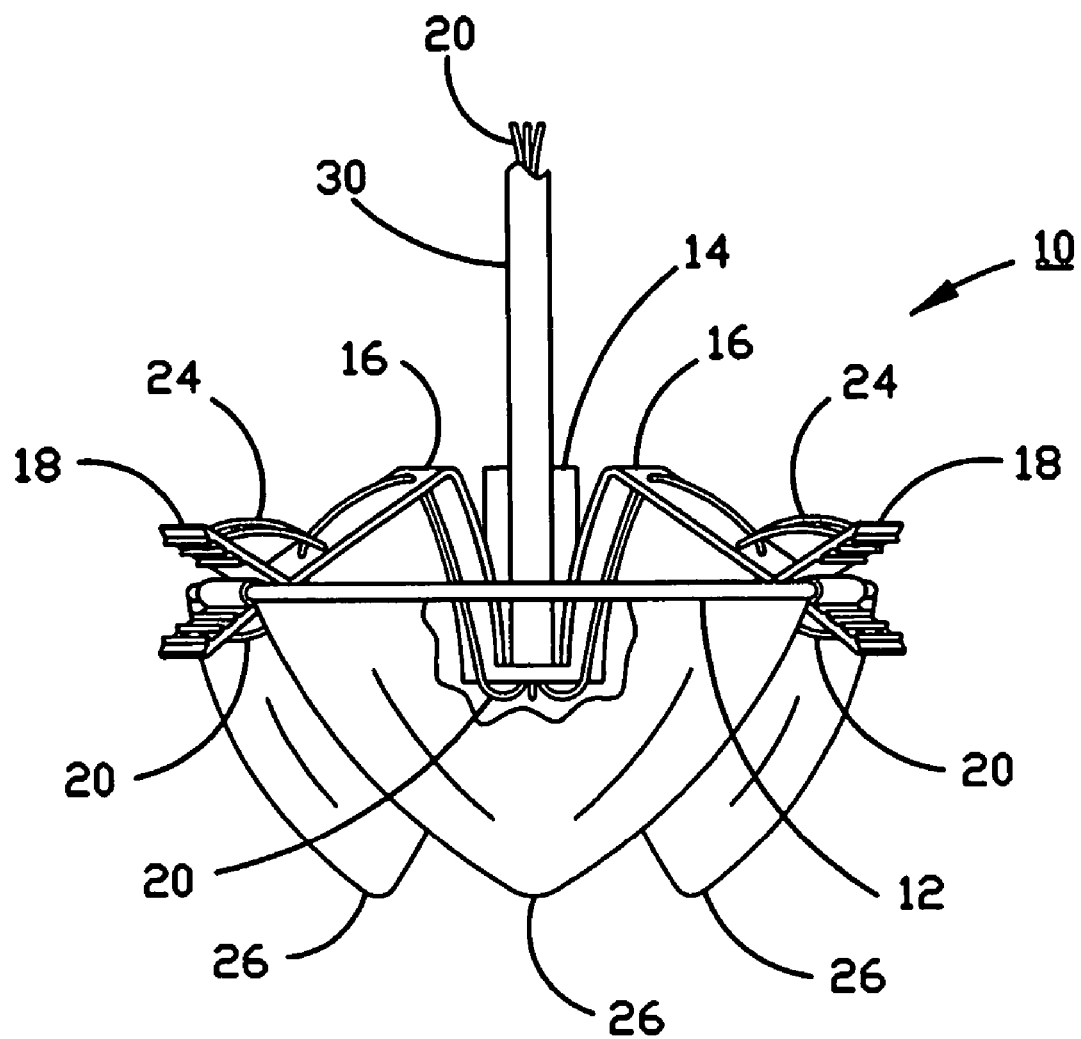
FIG. 4 illustrates the bistable heart valve prosthesis of FIG. 3 after the filaments have been pulled to cause legs of the heart valve prosthesis to elastically invert like an umbrella from the stable position of FIG. 3A to a second stable (inverted) position.

FIGS. 1A and 1B together illustrate a side view of a bistable heart valve prosthesis 10 in accordance with an embodiment of the invention. As illustrated, the heart valve prosthesis 10 includes an annular ring 12 that is connected to a body member 14 via legs 16 (FIG. 1B). In the illustrated embodiment, the legs 16 connect to the annular ring 12 via claws 18 that open and close in response to tensioning or pulling of filaments 20. As shown, the filaments connect to respective sides of claws 18 so that pulling of the filaments 20 from a remote location causes the claws 18 to be pulled from an initial relaxed (strain-free) position (FIG. 1) to the second stable (but not strain-free) position (FIG. 4). Pulling the filaments further causes the heart valve prosthesis 10 to deform more and to move to a position in which a second set of short, fixed length filaments 24 become taut. Pulling the filaments 20 even more causes the lower claw 18 to move down, while the upper claw 18 is held fixed by the taut filaments 24. This relative motion causes the claws 18 to open (FIG. 5) to allow ingress of tissue for grasping. Each claw 18 is connected to the annular ring and/or a leg 16 so as to permit movement of each claw 18 from the first (relaxed) position to the second (open) position. For example, as shown in FIGS. 1A and 1B, the claws 18 may be connected to the legs and to the annular ring 12 through a hole in the legs that permits the annulus 12 to slide in the hole. Each claw 18 is controlled by a filament 20 whereby the claws 18 may be opened in unison or independently, depending upon the filament 20 connections.

The filaments 20 are weaved through holes 22 in the legs 16 and through the center of the body member 14, thereby providing stability and, as will be illustrated in connection with FIG. 4, a mechanism for inverting the body member 14 from its stable position of FIG. 1 to another stable position (FIG. 4) for implantation. As best shown in FIG. 1B, small filaments 24 are used to hold one side of the claw 18 so that when the other side of the claw 18 is pulled using filament 20 the claws 18 open. Finally, at least two leaflets 26 are connected to the annular ring 12 in a conventional manner. It will be appreciated that, when the bistable heart valve prosthesis 10 is implanted, the existing chordae within the heart that connect the old native heart valve to the papillary muscles may function to help retain the leaflets 26 in the proper positions and to improve left ventricular function.

Figures 2A, 2B:
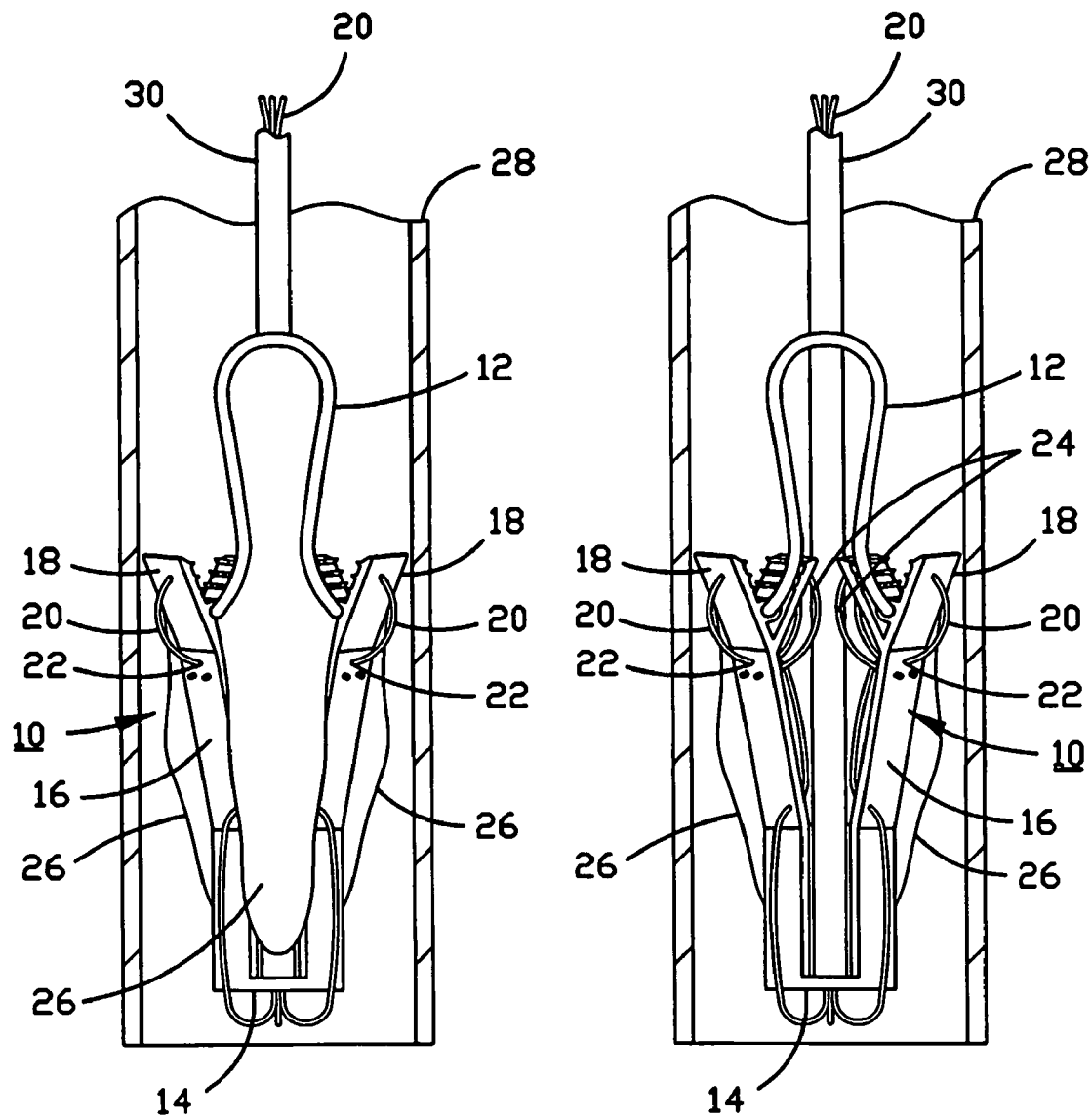
FIG. 2A illustrates the bistable heart valve prosthesis of FIG. 1 in a folded position and inserted into a catheter for delivery to the implantation position in the heart valve cavity.
FIG. 2B illustrates the bistable heart valve prosthesis of FIG. 2A with a leaflet cut away so that the folded body member, legs, annular ring, claws, and filaments may be seen more clearly.

FIGS. 2A and 2B together illustrate the bistable heart valve prosthesis 10 of FIG. 1 in a folded position and inserted into a catheter 28 for transseptal delivery to the implantation position in the heart valve cavity. As illustrated, a guiding mechanism 30, such as a smaller diameter guiding catheter attached to the heart valve prosthesis 10, is used to guide it through the catheter 28 and to guide the filaments 20 to a proximal end of catheter 28 for remote operation by the surgeon or other operator. Conversely, the filaments 20 may be attached to a single fastener (not shown) which, in turn, is attached to the distal end of the smaller diameter guiding catheter 30. The fastener may then be detachable (for example, by a microscrew) from the smaller diameter guiding catheter 30 for final release of the heart valve prosthesis 10 upon implantation.

Figure 3A:
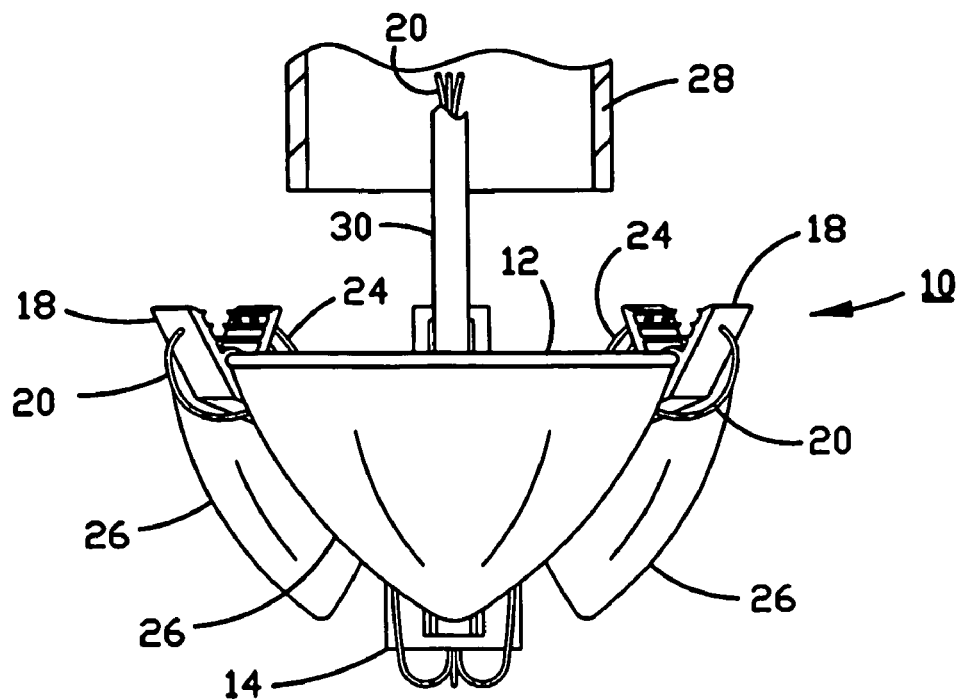
FIG. 3A illustrates a side view of the bistable heart valve prosthesis of FIG. 2 after it has emerged from the end of the catheter and elastically expanded to a first stable position.
Figure 3B:
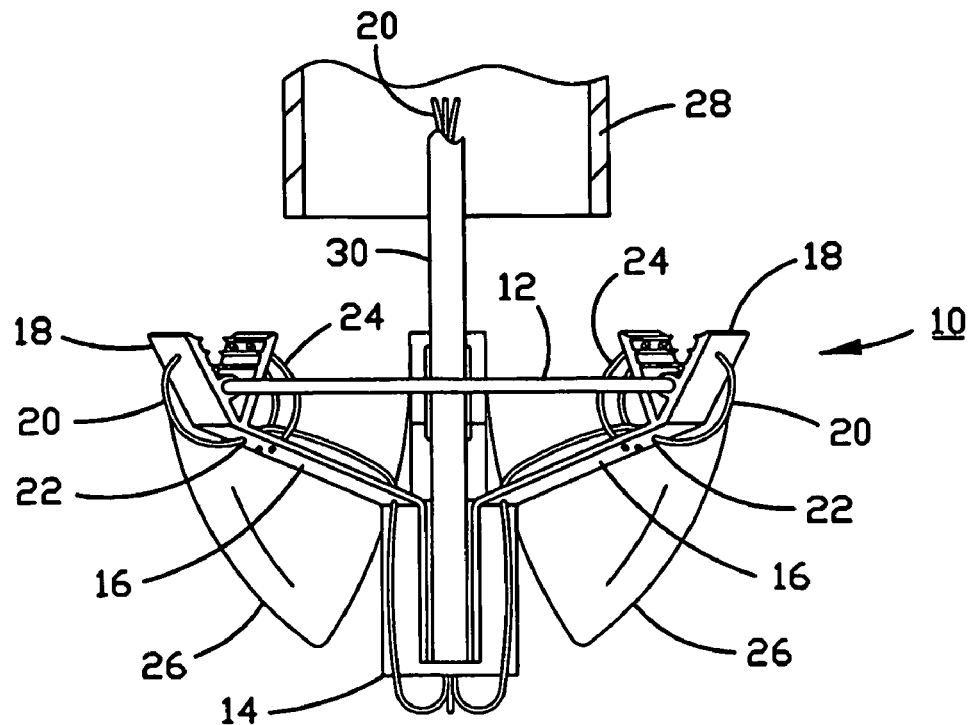
FIG. 3B illustrates the bistable heart valve prosthesis of FIG. 3A with a leaflet cut away so that the body member, legs, annular ring, claws, and filaments may be seen more clearly.

FIGS. 3A and 3B together illustrate a side view of the bistable heart valve prosthesis 10 of FIG. 2 after it has emerged from the end of the catheter 28 and elastically expanded to a first stable position. The body member 14 and annular ring 12 of the heart valve prosthesis 10 are preferably made of a sturdy but compliant, elastic material such as nitinol or a deformable plastic so that when the heart valve prosthesis 10 emerges from the distal end of the catheter 28, the body member 14 and annular ring 12 snap back to a first stable position (like a regular opened umbrella). It will be appreciated that the legs 16 may be curved to increase stiffness and arranged to bend in radially when in the collapsed position (FIGS. 2A and 2B). The legs 16 also may be tapered along their width to allow for minimal blockage of the blood flow once the heart valve prosthesis 10 is implanted. Although the illustrated embodiment has three legs 16 that are approximately symmetrically spaced (e.g., 120° apart), it will be appreciated that more or fewer legs and different spacings may also be used.

FIG. 4 illustrates the bistable heart valve prosthesis 10 of FIG. 3 after the filaments 20 have been pulled to cause the heart valve prosthesis 10 to elastically invert like an umbrella from the stable position of FIG. 3A to a second stable (inverted) position of FIG. 4. In other words, the body member 14 and legs 16 are sufficiently compliant such that when the filaments 20 are pulled with sufficient force, the body member 14 and legs to snap to the second stable position shown in FIG. 4. As will be explained in more detail below, this feature of the invention facilitates mounting of the heart valve prosthesis 10 in the heart valve cavity.

Figure 5:
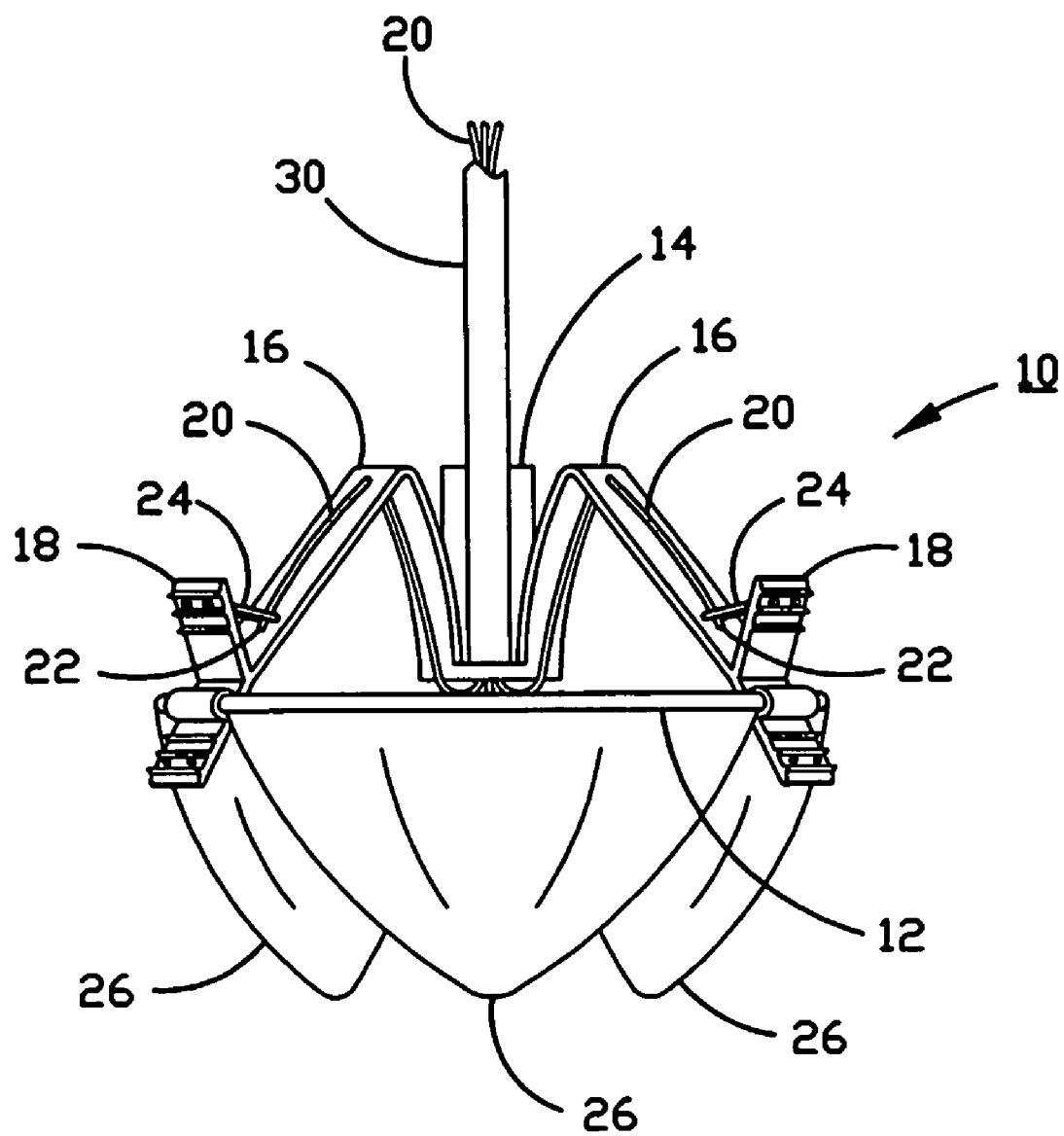
FIG. 5 illustrates the bistable heart valve prosthesis of FIG. 4 where more force is applied to the filaments to invert the legs past the second stable position, thereby causing the claws to open further for placement in the heart valve cavity.

FIG. 5 illustrates the bistable heart valve prosthesis 10 of FIG. 4 where more force is applied to the filaments 20 to cause the claws 18 to open further for placement in the heart valve cavity. As also shown, the body member 14 is moved from the second stable position of FIG. 4 to a more proximal, unstable position.

Figure 6:
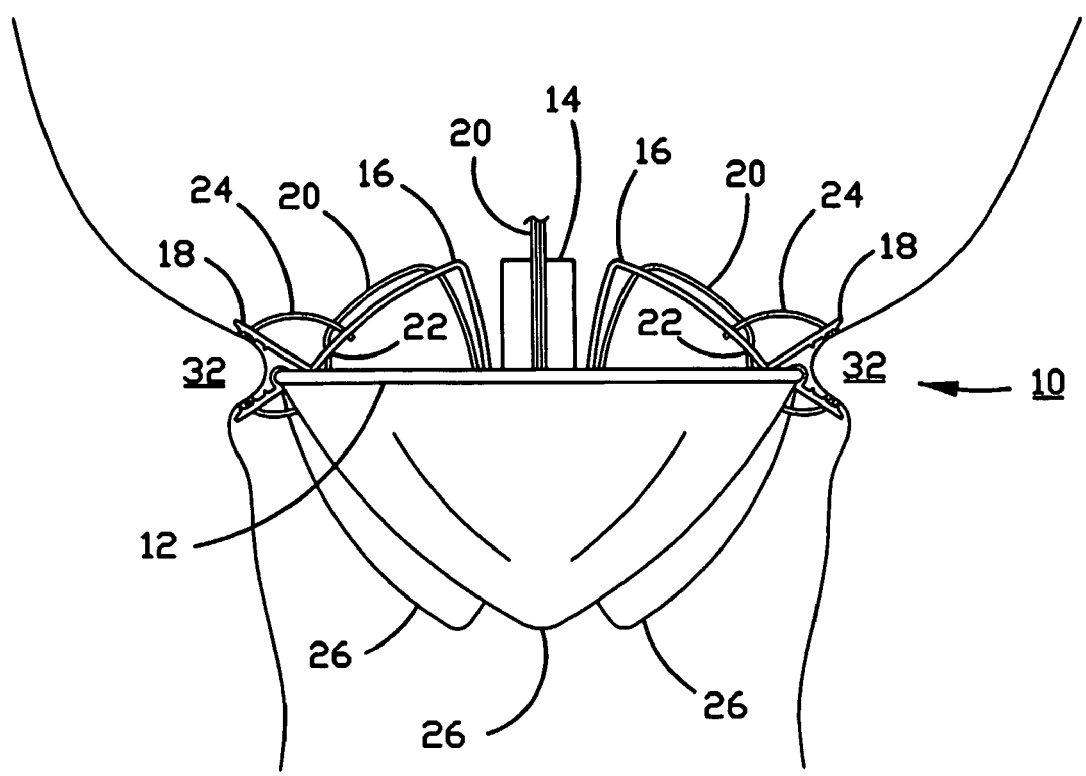
FIG. 6 illustrates the bistable heart valve prosthesis of FIG. 5 where the tension on the filaments has been removed and the claws have clamped down on adjacent heart tissue.

FIG. 6 illustrates the bistable heart valve prosthesis 10 of FIG. 5 where the tension on the filaments 20 has been removed once the heart valve prosthesis 10 is at the implantation position in the heart valve cavity and the claws 18 have clamped down on adjacent heart tissue 32.

The size (radius) of the heart valve prosthesis 10 is varied in accordance with whether the heart valve prosthesis 10 is to be used to repair or replace the mitral valve, the aortic valve, the pulmonary valve, or the tricuspid valve. These dimensions (typically 20-30 mm) may be readily determined by techniques known by those skilled in the art. All elements are then scaled accordingly. Also, those skilled in the art will appreciate that the heart valve prosthesis 10 may be mounted in a reverse fashion on the smaller diameter guiding catheter 30 for retrograde implantation at such other heart valve positions.

The surgical procedure for implanting the bistable percutaneous heart valve prosthesis 10 will now be described with respect to FIGS. 7-12 for the example of implantation of a mitral valve prosthesis. It will be understood from the following description that the catheter 28 would be placed at different positions with respect to the valve cavities in the event that the heart valve prosthesis to be implanted is a prosthetic pulmonary valve, tricuspid valve, or aortic valve. Also, noted above, the heart valve prosthesis 10 would have different dimensions for the different implantation positions.

Figure 7:
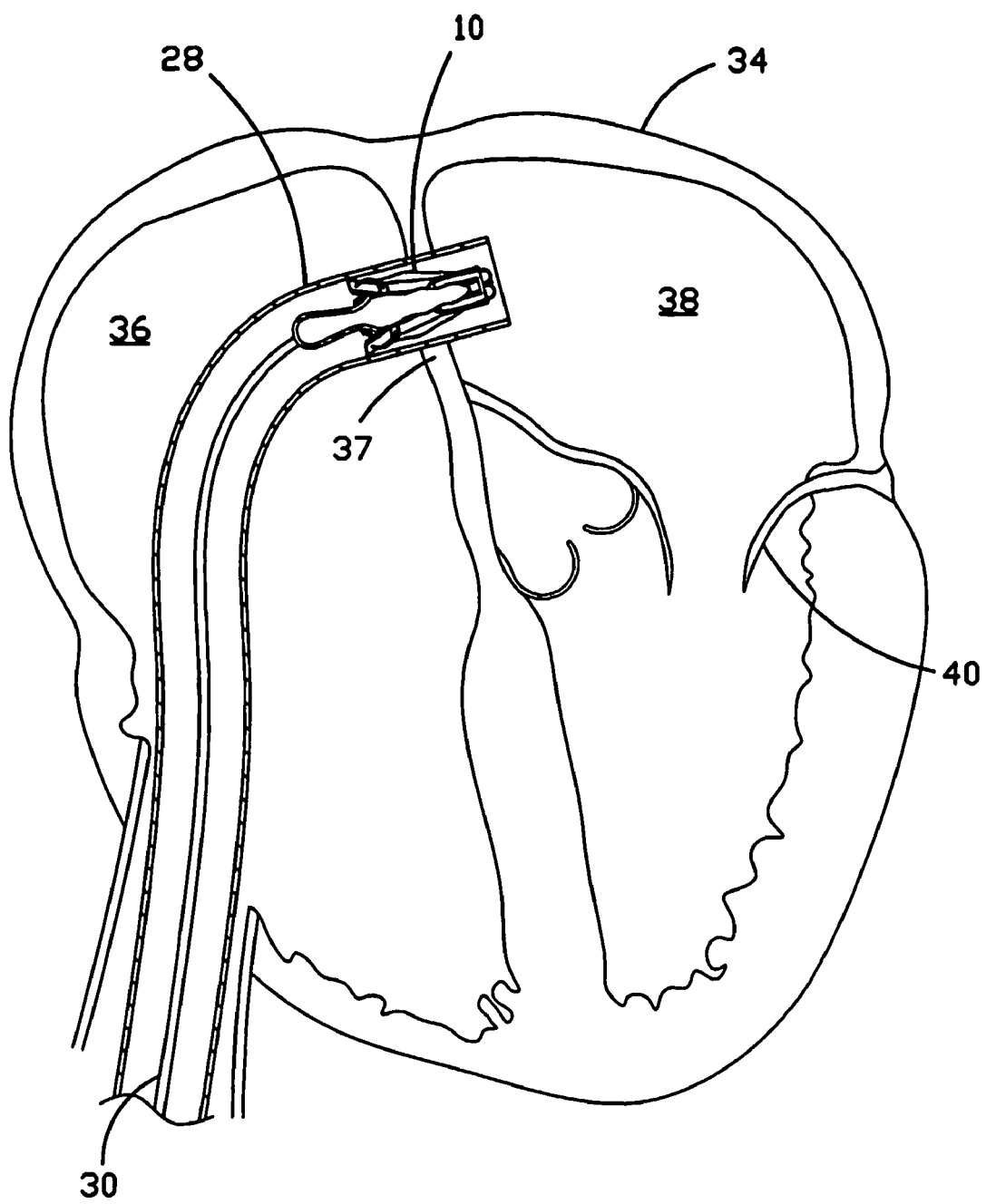
FIG. 7 illustrates the placement of a catheter with a folded mitral valve prosthesis therein above the mitral valve prior to implantation.

To implant the heart valve prosthesis 10, during surgery the heart valve prosthesis 10 described above with respect to FIGS. 1-6 is folded into its collapsed position (FIGS. 2A and 2B) and a catheter 28 with a suitably sized lumen for accepting the folded heart valve prosthesis 10 is inserted into the patient and guided in a conventional fashion to a position adjacent an implantation position in a patient's heart (for example, adjacent the mitral valve, the pulmonary valve, the tricuspid valve, or the aortic valve). Once the catheter 28 is in place, the folded heart valve prosthesis 10 is inserted into the catheter 28 and guided to the distal end of the catheter 28 using a smaller diameter guiding catheter 30. In turn, the smaller diameter guiding catheter 30 may accept a guide wire (not shown) for guiding the smaller diameter guiding catheter 30 through the catheter 28 and the heart chambers. As shown in FIG. 7, the catheter 28 enters the heart 34 via the inferior vena cava or superior vena cava, passes through the right atrium 36, across the interatrial septum 37, and into the left atrium 38 above the mitral valve 40.

Figure 8:
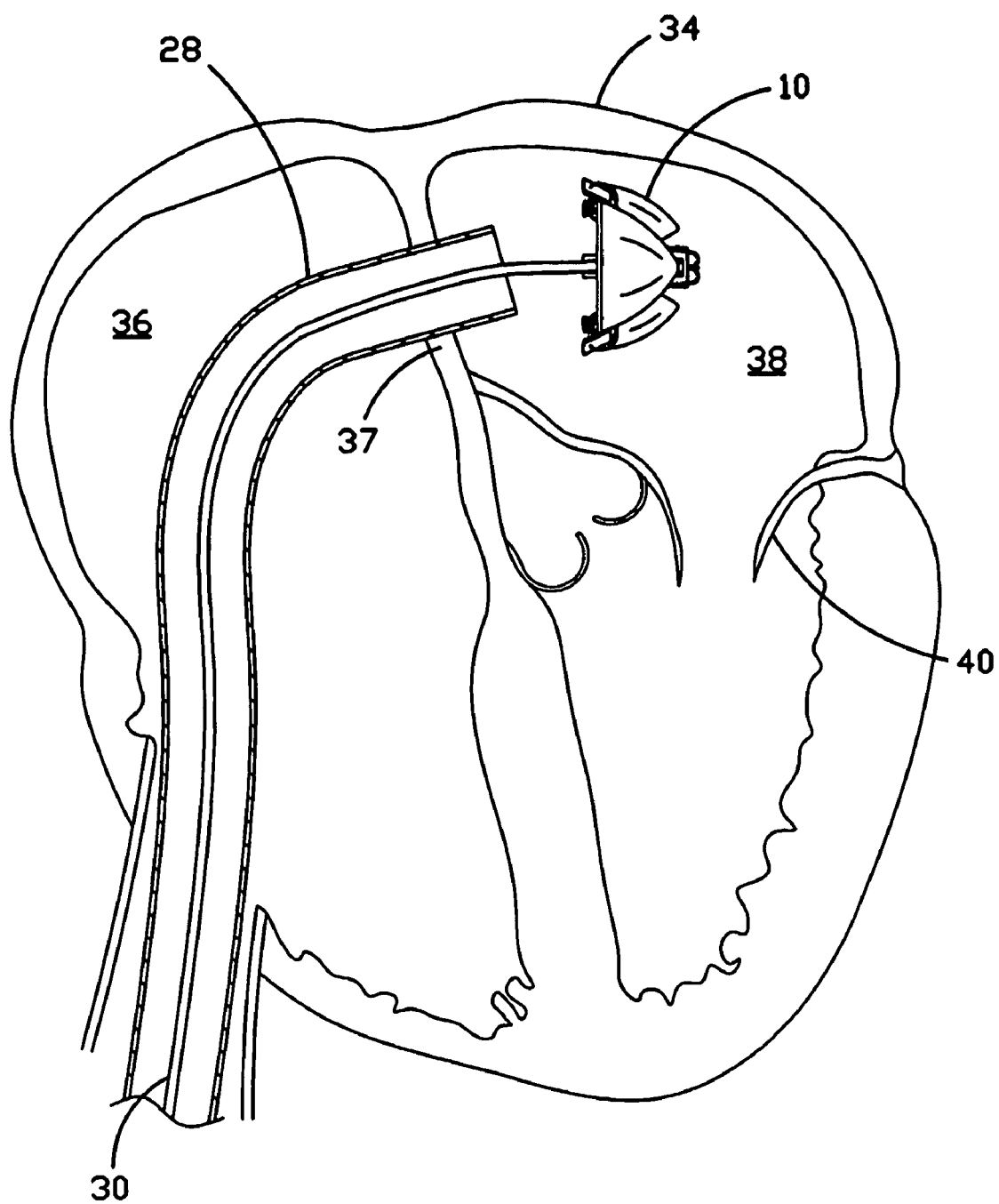
FIG. 8 illustrates the unfolded mitral valve prosthesis in a first stable position within the left atrium.
Figure 9:
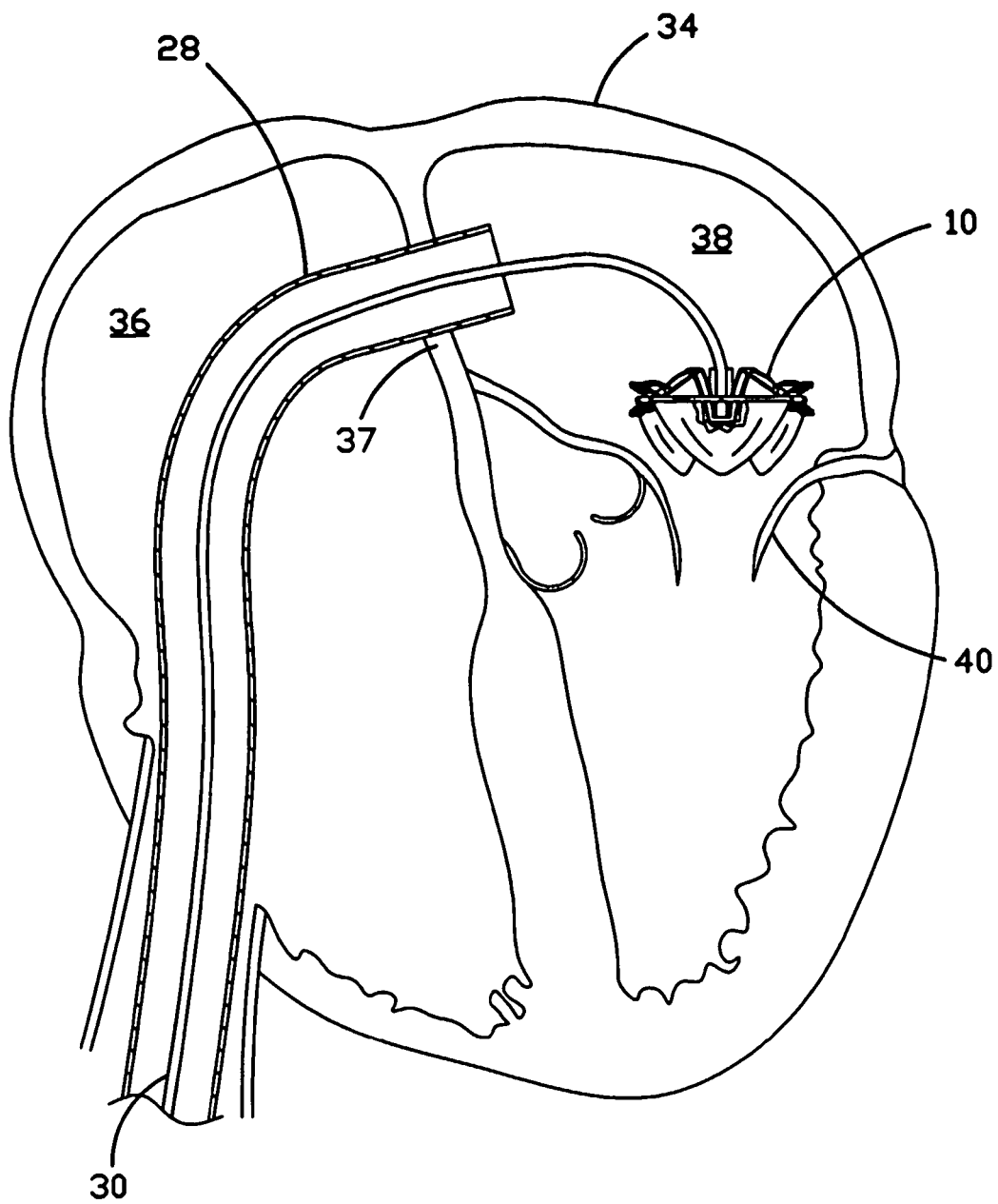
FIG. 9 illustrates the mitral valve prosthesis in a second stable position within the left atrium after the legs have been inverted by pulling the filaments attached to the body member.

Once the catheter 28 is in place and the heart valve prosthesis 10 has been guided to the distal end of the catheter 28, the heart valve prosthesis 10 is unfolded to a first stable position by pushing it out of the distal end of the catheter 28 (FIG. 8). Generally, the natural elasticity of the annular ring 12 and body member 14 causes the heart valve prosthesis 10 to snap to this first stable position once it is beyond the end of the catheter 28. The heart valve prosthesis 10 is then "snapped-through" from this first stable position to a second stable position by pulling on the filaments 20 as described above. The "snapped-through" heart valve prosthesis 10 is illustrated in FIG. 9.

Figure 10:
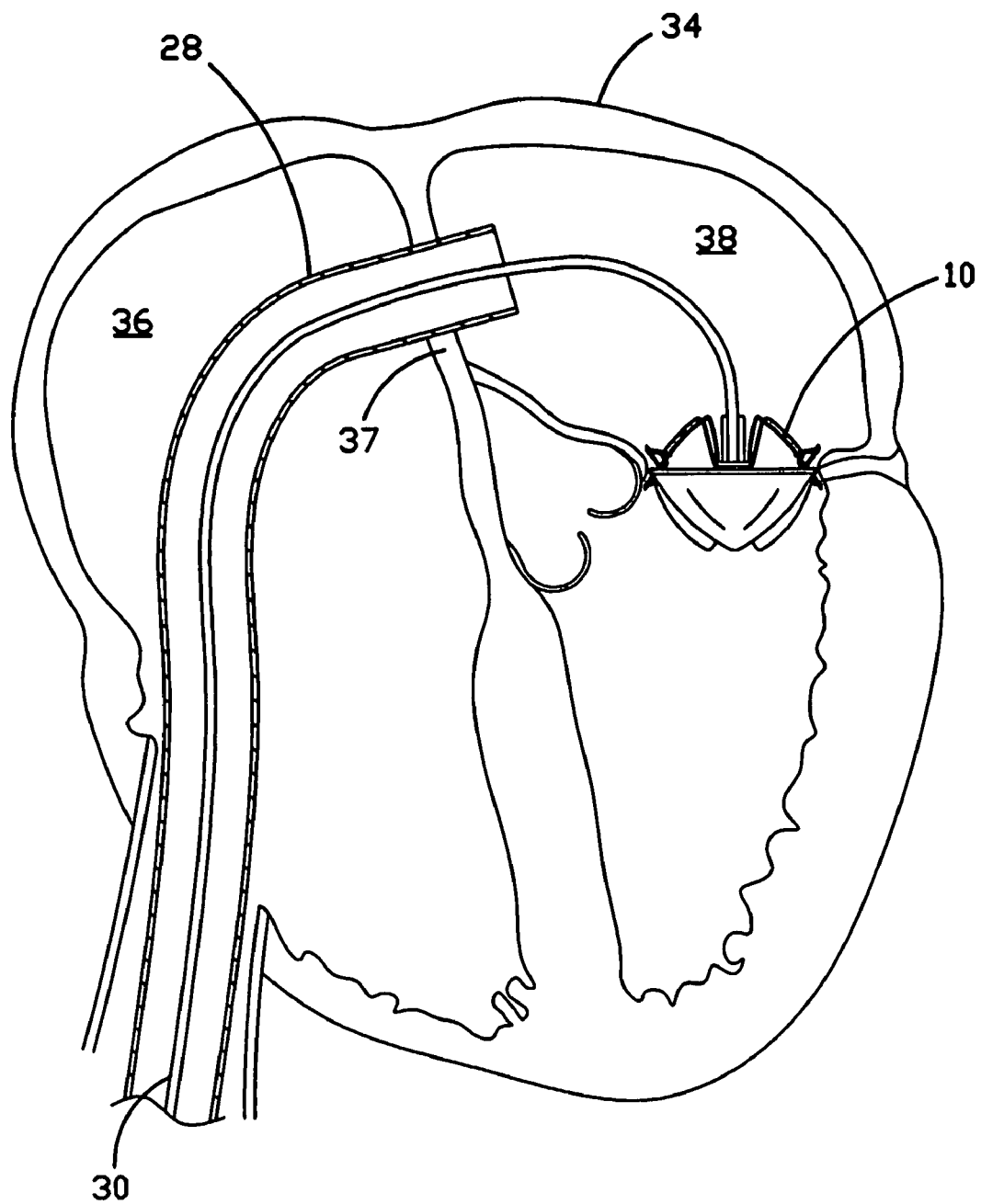
FIG. 10 illustrates the mitral valve prosthesis in the second stable position as it is guided to the implantation position (e.g., valve seat).
Figure 11:
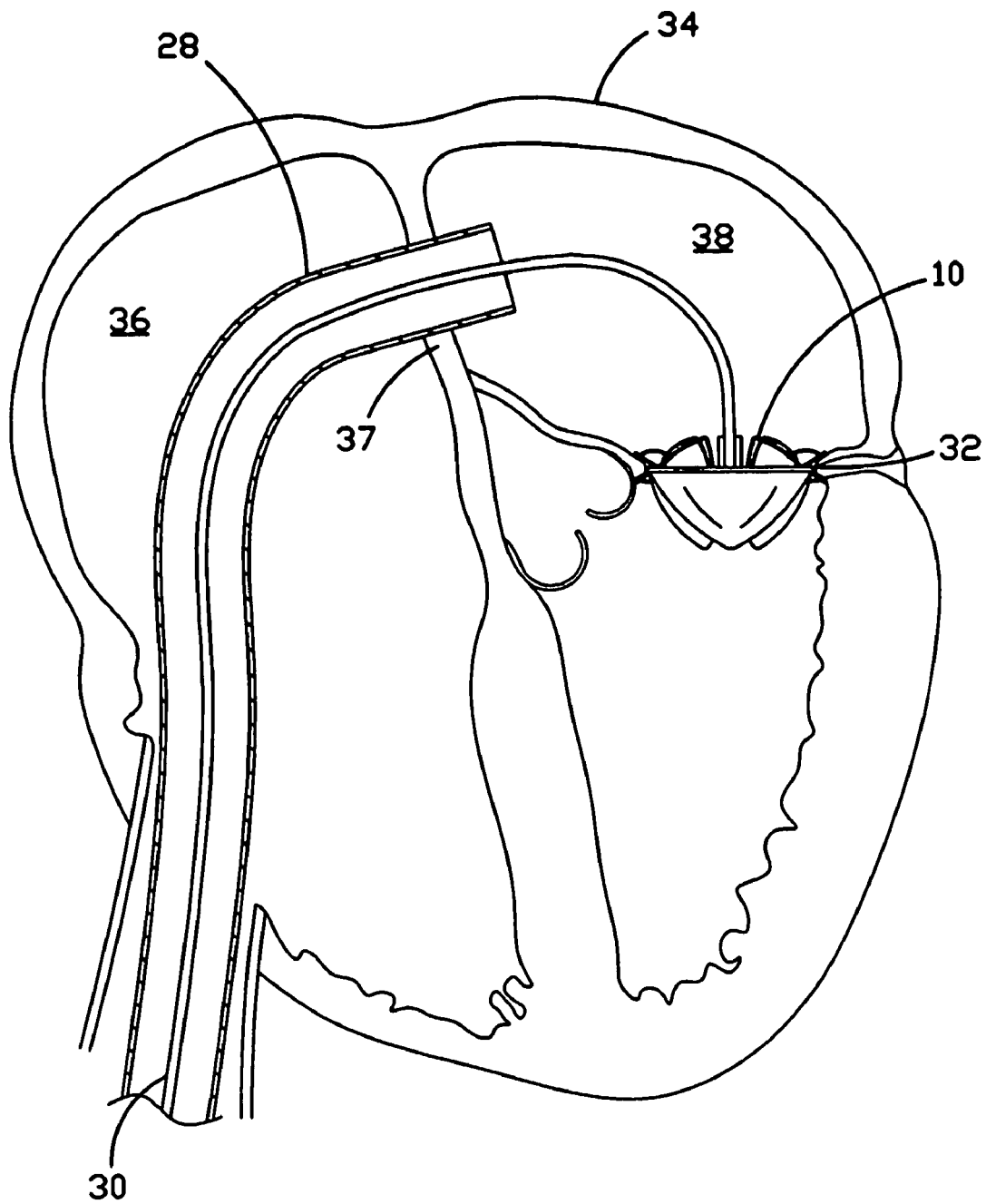
FIG. 11 illustrates the mitral valve prosthesis at its implantation position in the mitral valve cavity once tension from the filaments has been removed to cause the claws to clamp down on any of the surrounding heart tissue now within the open claws.
Figure 12:
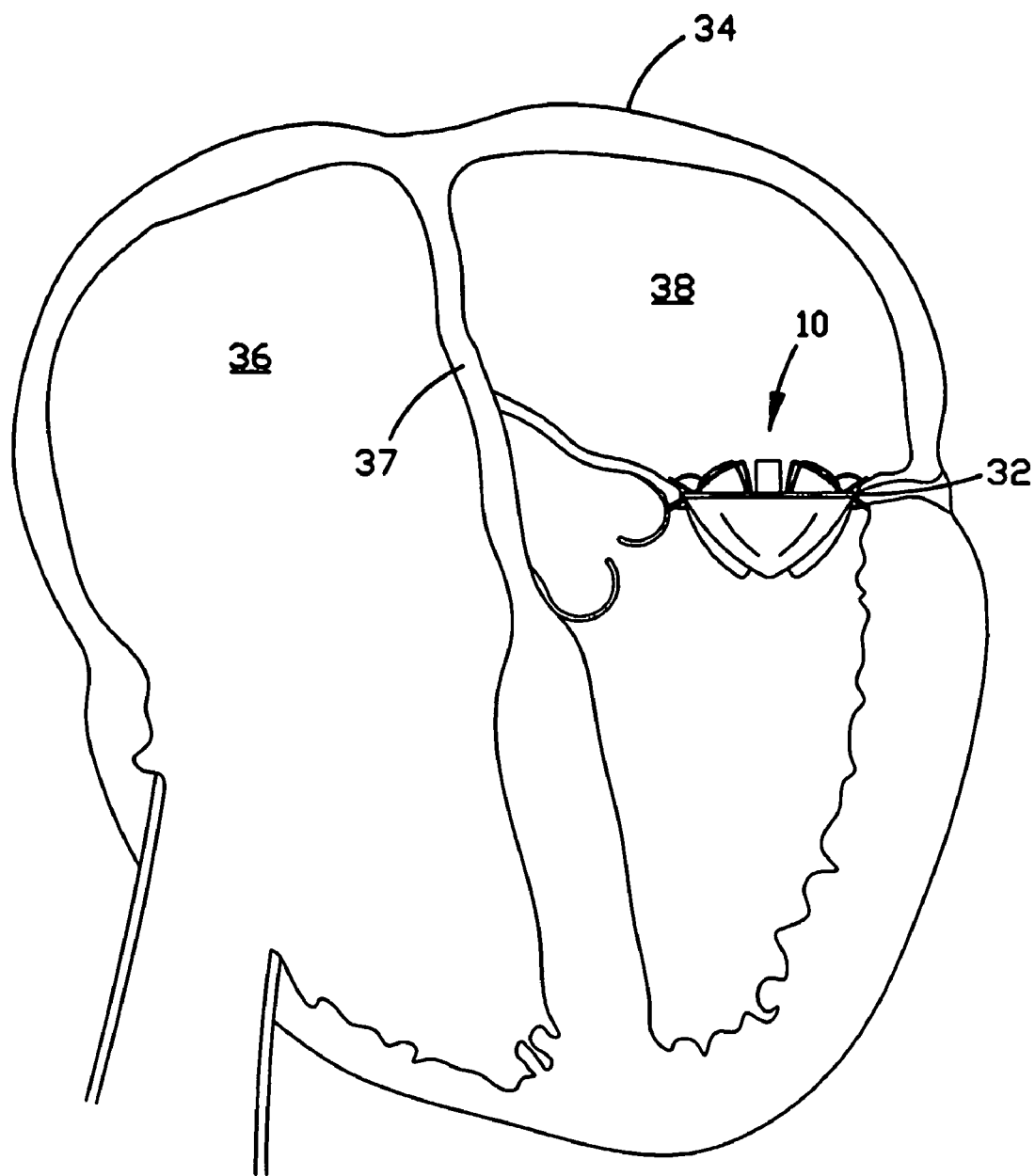
FIG. 12 illustrates the heart valve prosthesis in its implanted position with the catheter removed.

The heart valve prosthesis 10 in the second stable position is then guided to the implantation position (e.g., valve seat) as shown in FIG. 10 using the smaller diameter guiding catheter 30. Imaging devices (not shown) may be used to permit the surgeon (operator) to watch the movement of the heart valve prosthesis 10 to the implantation position. Tension on the filaments 20 and 24 is released once the heart valve prosthesis 10 is in position (FIG. 10), thereby releasing the tension holding open the claws 18 and deforming the body member 14. As shown in FIG. 11, removing the tension from the filaments 20 causes the claws 18 to clamp closed in their snapped equilibrium position, thereby clamping down on any of the surrounding heart tissue 32 now disposed within the claws 18. The filaments 20 are again locked to the catheter 28. The steps of releasing the tension on filament 20 and pushing the heart valve prosthesis 20 to cause deformation may be conducted simultaneously. The surgeon (operator) may continue to push down on the heart valve prosthesis 10 and checking the stability of the implantation of the heart valve prosthesis 10 until it is determined that the heart valve prosthesis 10 is stably implanted and that the claws 18 "bite" sufficiently into the heart tissue 32. These steps of pushing down on the heart valve prosthesis 10 and checking the "bite" of the claws 18 may be reversed and repeated for one or all of the claws 18 until the location and orientation of the heart valve prosthesis 10 and stability of implantation are acceptable. When properly placed, the claws 18 maintain a tight grip on the heart tissue 32 so as to hold the heart valve prosthesis 10 in place. It also will be appreciated that once the filaments 20 and 24 are released and allowed to become slack that the legs 16 will have opened out radially into their final positions. The filaments 20 are then released from the smaller diameter guiding catheter 30 by, for example, unscrewing a microscrew, and the smaller diameter guiding catheter 30 is slowly disengaged from the body member 14. It is noted that the heart valve prosthesis 10 may move a bit during this disengagement to adjust to the new boundary conditions. This should not be a problem so long as the claws 18 have a suitable grip on the heart tissue 32. However, it will be appreciated that if the operator observes too much movement of the implanted heart valve prosthesis 10 that the catheter 28 may be used to push down on the heart valve prosthesis 10 to recheck the implantation stability. Thus, unlike balloon expandable devices with stents, the heart valve prosthesis 10 described herein is redeployable and may be positively, as opposed to passively, anchored. The catheter 28 and the smaller diameter guiding catheter 30 are then extracted. FIG. 12 illustrates the heart valve prosthesis 10 in its implanted position with the catheter 28 removed.

It will be appreciated that as the heart valve prosthesis 10 is being pushed down to be seated in the valve cavity that the elasticity of the annular ring 12 permits it to be distorted to the shape of the non-circular ring profile of the implantation position in the valve cavity. Typically, most of the shape distortion is in the plane of the annular ring 12. The elasticity of the annular ring 12 causes it to push radially against the heart tissue 32 at the implantation position as the annular ring 12 attempts to spring back to its original annular shape. The resulting elastic force functions to hold the heart valve prosthesis 10 in position. It will be further appreciated that, once implanted, the body member 14 in its inverted stable position also has great stability and strength (like an inverted umbrella) and pushes outward on the annular ring 12 so as to further assist anchoring the heart valve prosthesis 10 in the heart tissue 32.

Although implementations of the invention have been described in detail above, those skilled in the art will readily appreciate that many additional modifications are possible without materially departing from the novel teachings and advantages of the invention. For example, those skilled in the art will appreciate that the body member, legs, and claws may be integrated into a one-piece design for reliability, safety, and ease of manufacture. As another example, the filaments 24 may be replaced by a motion restraint such as a protrusion that contacts either the legs 16 or either side of the claws 18 to limit movement. Any such modifications are intended to be included within the scope of the invention as defined in the following claims.

What is claimed:

1. A bistable percutaneous heart valve, comprising:
an elastic annular ring;
a body member having a plurality of legs, each leg connecting at one end to said annular ring;
at least two claws that are adjustable from a first position to a second position by application of external force so as to allow ingress of surrounding heart tissue into said claws in said second position, wherein upon removal of the external force the claws elastically revert to the first position so as to grip the heart tissue positioned within the claws, thereby holding said heart valve in place; and
at least one leaflet membrane connected to at least one of said annular ring, said body member and said legs, said at least one leaflet membrane having a first position for blocking blood flow therethrough and a second position for allowing blood flow therethrough.

2. A heart valve as in claim 1, wherein said annular ring is adapted to fit in a mitral valve opening of a heart.

3. A heart valve as in claim 1, wherein said annular ring is adapted to fit in an aortic valve opening of a heart.

4. A heart valve as in claim 1, wherein said annular ring is adapted to fit in a pulmonary valve opening of a heart.

5. A heart valve as in claim 1, wherein said annular ring is adapted to fit in a tricuspid valve opening of a heart.

6. A heart valve as in claim 1, wherein said annular ring, said body member, said legs, said claws and said at least one leaflet membrane fold into a collapsed position for insertion into a catheter for percutaneous delivery to the heart for implantation.

7. A heart valve as in claim 6, wherein said heart valve has a first stable position after passage through the catheter and a second stable position to which the heart valve is forced for implantation.

8. A heart valve as in claim 7, wherein said body member and legs push outward on said annular ring in said second stable position so as to assist anchoring said heart valve in said heart tissue.

9. A heart valve as in claim 1, wherein said annular ring is expandable radially to anchor the heart valve at an implantation position.

10. A heart valve as in claim 7, wherein each claw is connected to at least one of said annular ring and a leg so as to permit movement of each claw from said first position to said second position.

11. A heart valve as in claim 1, wherein further comprising at least one filament connecting said body member to said claws, said filament extending proximally from said heart valve so as to permit control of said claws between said first and second positions from a location remote from an implantation position of said heart valve.

12. A heart valve as in claim 11, further comprising a motion restraint that restrains one side of said claws while said at least one filament is connected to another side of said claws, whereby pulling said at least one filament causes the claws to open.

13. A heart valve as in claim 1, wherein said body member and claws are integrated into a one-piece design.

14. A bistable percutaneous heart valve, comprising:
an expandable elastic annular ring;
a body member having a plurality of legs, each leg connecting at one end to said annular ring;
at least two claws that are adjustable to guide said heart valve to an implantation position; and
at least one leaflet membrane connected to at least one of said annular ring, said body member and said legs, said at least one leaflet membrane having a first position for blocking blood flow therethrough and a second position for allowing blood flow therethrough,
wherein said expandable annular ring expands to anchor said heart valve at said implantation position.

15. A heart valve as in claim 14, wherein said annular ring, said body member, said legs, said claws and said at least one leaflet membrane fold into a collapsed position for insertion into a catheter for percutaneous delivery to the implantation position.

* * * * *